United States Patent [19]

DelMar

[11] Patent Number: 4,507,513

[45] Date of Patent: Mar. 26, 1985

[54] CATALYZED GRIGNARD COUPLING PROCESS

[75] Inventor: Eric G. DelMar, Hopewell, N.J.

[73] Assignee: FMC Corporation, Philadelphia, Pa.

[21] Appl. No.: 575,131

[22] Filed: Jan. 30, 1984

[51] Int. Cl.³ .............................................. C07C 17/26
[52] U.S. Cl. ................................................... 570/190
[58] Field of Search ......................................... 570/190

*Primary Examiner*—Anton H. Sutto
*Assistant Examiner*—Joseph A. Boska
*Attorney, Agent, or Firm*—R. L. Hansen; H. R. Ertelt

[57] ABSTRACT

A 3-halo-2-methylphenylmagnesium halide is cross-coupled with a halobenzene using nickel(II) acetylacetonate as catalyst, producing a 3-halo-2-methyl[1,1'-biphenyl]. The amount of catalyst should be greater than 0.01 mole percent, but not more than 0.1 mole percent, based on the 3-halo-2-methylphenylmagnesium halide to achieve the best yields.

1 Claim, No Drawings

CATALYZED GRIGNARD COUPLING PROCESS

This invention is in the field of chemical processes; more specifically, cross-coupling an aryl Grignard reagent with a halobenzene in the presence of a catalyst to produce a biphenyl compound.

Pyrethroid ester insecticides are of great commercial interest throughout the world. Both the carboxylic acid and alcohol moieties of these esters cover a wide range of structures. The alcohol, (2-methyl[1,1'-biphenyl]-3-yl)-methanol, affords a series of esters having especially attractive insecticidal efficacy when combined with appropriate carboxylic acids; for example, 3-(2,2-dihaloethenyl)-2,2-dimethylcyclopropanecarboxylic acids and 3-(2-chloro-3,3,3-trifluoro-1-propenyl)-2,2-dimethylcyclopropanecarboxylic acid. Esters of these acids combined with (2-methyl[1,1'-biphenyl]-3-yl)-methanol are described in U.S. Pat. No. 4,214,004 and U.S. Pat. No. 4,238,505, respectively, the disclosures thereof being incorporated herein by reference.

Although pyrethroid esters of (2-methyl[1,1'-biphenyl]-3-yl)-methanol have commercial potential, yields of the requisite (2-methyl[1,1'-biphenyl]-3-yl)-methanol from known preparative techniques have been too low to warrant commercialization. For example, U.S. Pat. No. 4,214,004 discloses an overall yield of about 15% beginning with 2-methyl-3-nitrobenzyl alcohol.

According to the multistep synthesis of which the present invention is the key step, the overall yield of (2-methyl[1,1'-biphenyl]-3-yl)-methanol is about 60% utilizing a commercially available 2,6-dihalotoluene, e.g., 2,6-dichlorotoluene or 2-bromo-6-chlorotoluene, in the first step to produce a 3-halo-2-methylphenylmagnesium halide, i.e., 3-chloro-2-methylphenylmagnesium chloride or bromide, by conventional techniques. The 2,6-dihalotoluene preferably carries at least one chlorine atom in order to minimize self-coupling.

The key to success of the overall process lies in the next step in which the 3-halo-2-methylphenylmagnesium halide dissolved in an inert solvent is cross-coupled with a halobenzene in the presence of a catalytic amount of nickel(II) acetylacetonate, producing a 3-halo-2-methyl-[1,1'-biphenyl], e.g., 3-chloro-2-methyl-[1,1'-biphenyl]. It is this step which is the process of this invention.

Coupling reactions of Grignard reagents are known to lead to mixtures of products because of the possibilities for both homo and hetero coupling between the reactants, as well as coupling between the reactants and products. The products from attempted cross-coupling of a Grignard reagent with a halocarbon compound often constitute an intractable mixture with a low yield of the desired cross-coupled product.

It is known that the cross-coupling reaction can be enhanced selectively by the addition of transition metal salts or coordination complexes; for example, use of nickel(II) salts and complexes has been reviewed by Kumada, *Pure and Appl. Chem.*, 52, 669 (1980). The catalytic activity of nickel(II) complexes in a given reaction depends strongly upon both the specific reactants and the nature of the ligands in the complex, however; see Tamao, et al., *Bull. Chem. Soc. Japan*, 49, 1958 (1976), who reported nickel(II) acetylacetonate "showed no activity at all for the coupling of simple alkyl Grignard reagents with chlorobenzene."

Nickel(II) acetylacetonate has affected other cross-coupling reactions, however. Mitchell and Yan, *Can. J. Chem.*, 58, 2584 (1980), reported yields of 35–60%, 3,3"-dichloro-2,2"-dimethyl-o-terphenyl in the cross-coupling of 3-chloro-2-methylphenylmagnesium chloride with o-dibromobenzene in tetrahydrofuran using equivalent amounts of the reactants and 6 mole percent nickel(II) acetylacetonate based on the Grignard reagent. Ibuki, et al., *Bull. Chem. Soc. Japan*, 53, 821 (1980), reported cross-coupling two-fold excess phenylmagnesium bromide with 2-iodobiphenyl in the presence of 1.0% nickel(II) acetylacetonate based on the limiting reagent, obtaining a 78–80% yield of o-terphenyl. Clough, et al., *J. Org. Chem.*, 41, 2256 (1976), reported cross-coupling an eight-fold excess of phenylmagnesium iodide with 1,8-diiodonaphthalene using 0.9 mole percent nickel(II) acetylacetonate based on the limiting reagent, producing 1,8-diphenylnaphthalene in 70% yield, while Corriu and Masse, *J. Chem. Soc. Chem. Comm.*, 144 (1972), reported yields of 40 to more than 80% in cross-coupling reactions utilizing 0.1–1 percent nickel(II) acetylacetonate with respect to Grignard reagent.

On the basis of the prior art, cross-coupling a 3-halo-2-methylphenylmagnesium halide with a halobenzene using nickel(II) acetylacetonate as catalyst would seem to be best carried out by using about 1 mole percent nickel(II) acetylacetonate based on the limiting reagent and perhaps a molar excess of the Grignard reagent. One would expect to obtain a yield of 60–80%, 3-halo-2-methyl-[1,1'-biphenyl]. Nothing in the prior art suggests an increase in the yield to about 90% by decreasing the catalyst level one to two orders of magnitude, but therein lies the present invention.

In a process for producing a 3-halo-2-methyl-[1,1'-biphenyl] by cross-coupling a halobenzene with a 3-halo-2-methylphenylmagnesium halide in an inert solvent using nickel(II) acetylacetonate as catalyst, the present invention is the improvement which comprises using a catalytic amount of said catalyst greater than 0.01 mole percent, but not more than 0.1 mole percent, based on the 3-halo-2-methylphenylmagnesium halide.

The 3-halo-2-methyl-[1,1'-biphenyl] cross-coupling product can be converted to the desired (2-methyl[1,1'-biphenyl]-3-yl)-methanol by various methods. For example, the 3-halo-2-methyl[1,1'-biphenyl] can be converted to a second Grignard, a 2-methyl([1,1'-biphenyl]-3-yl)magnesium halide, which then yields the desired (2-methyl-[1,1'-biphenyl]-3-yl)-methanol when treated with formaldehyde, processes which are well known in the art.

Although other techniques for preparing the Grignard reagent are known, the 3-halo-2-methylphenylmagnesium halide, preferably 3-chloro-2-methylphenylmagnesium chloride, is advantageously prepared in an inert solvent. Inert solvents suitable for use in the process include ethers, e.g., tetrahydrofuran and diethyl ether. Tetrahydrofuran is preferred when preparing 3-chloro-2-methylphenylmagnesium chloride, at least two moles of tetrahydrofuran per mole of Grignard reagent.

The so-prepared solution of the Grignard reagent may be added to a warm, stirred mixture of the catalyst in the halobenzene, or the halobenzene may be added to a warm (50° to 80° C. preferred), stirred mixture of the catalyst and solution of the Grignard reagent. The rate of addition is not critical, but relatively fast addition, i.e., 0.5 to 1.0 hr., is advantageously employed. The reaction generally is completed in a few hours.

Whereas the halobenzene may be bromobenzene or iodobenzene, bromobenzene is preferred. At least a 10% molar excess of halobenzene is preferably used to minimize coupling of the Grignard reagent to the product. The use of iodobenzene leads to more self-coupling to biphenyl, with a corresponding decrease in cross-coupling yield, than if bromobenzene is used.

A catalytic amount of nickel(II) acetylacetonate, greater than 0.01 mole percent, but not more than 0.1 mole percent based on the Grignard reagent should be used, with the 0.02–0.04 mole percent range being preferred for maximum yields.

The procedure for preparing the Grignard reagent and conducting the cross-coupling reaction of this invention are illustrated in the following Example.

EXAMPLE 1

Under a dry nitrogen atmosphere, a stirred mixture of magnesium turnings (97.3 g, 4.00 moles) in approximately 65 ml of dry tetrahydrofuran was heated to 65° C. To the warm mixture was added one ml of 1,2-dibromoethane. While maintaining the temperature at about 65° C., a solution of 2,6-dichlorotoluene (322 g, 2.00 moles) in dry tetrahydrofuran (600 ml) was added to the mixture during a 45 minute period. After complete addition, the reaction mixture was stirred at 65° C. for three hours. Analysis of the reaction mixture indicated each milliliter of the solution contained 1.698 milliequivalents of 3-chloro-2-methylphenylmagnesium chloride.

Under a dry nitrogen atmosphere, 50 ml of the above-described reaction mixture, containing 0.085 mole 3-chloro-2-methylphenylmagnesium chloride, was stirred and heated at 50° C. Nickel(II) acetylacetonate hydrate (0.00825 g, 0.00003 mole) was added to the mixture. During a one hour period bromobenzene (18.8 g, 0.120 mole) was added dropwise to the warm reaction mixture. After complete addition, the mixture was stirred at 50° C. for 23 hours. The mixture was cooled to room temperature and 20.0 ml of n-tetradecane added as an internal standard for GLPC analysis. The resultant mixture was washed with 25 ml of a 0.1N hydrochloric acid solution. Analysis of the washed mixture by GLPC indicated 20.73% by weight of 3-chloro-2-methyl[1,1'-biphenyl], an 88.9% yield.

Other similar experiments, arranged in order of increasing amount of catalyst, are summarized as follows:

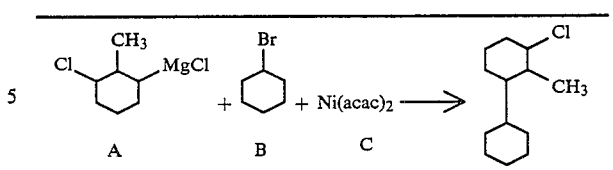

| Example | Reagents A (moles) | B (moles) | $C^a$ (mole %) | Addition Time (hr) | Reaction$^b$ Time (hrs) | Reaction$^b$ Temp (°C.) | Yield (%) |
|---|---|---|---|---|---|---|---|
| 2* | 0.10 | 0.11 | 0.01 | 0.17 | 22.0 | 89 | 66.6 |
| 3 | 0.085 | 0.12 | 0.024 | 2.0 | 24.0 | 65 | 84.3 |
| 4 | 0.085 | 0.12 | 0.024 | 1.5 | 24.0 | 80 | 85.0 |
| 5 | 0.085 | 0.12 | 0.024 | 1.5 | 24.0 | 50 | 86.2 |
| 6 | 0.085 | 0.12 | 0.024 | 1.0 | 24.0 | 65 | 86.2 |
| 7$^c$ | 0.048 | 0.0528 | 0.02 | 0$^d$ | 9.0 | 80 | 87.8 |
| 8$^c$ | 1.0 | 1.1 | 0.02 | 0.17 | 3.0 | 25–80 | 88.2 |
| 9$^c$ | 0.032 | 0.0352 | 0.02 | 0.75 | 4.0 | 80 | 89.2 |
| 1 | 0.085 | 0.12 | 0.035 | 1.0 | 24.0 | 50 | 88.9 |
| 10 | 0.085 | 0.12 | 0.035 | 1.0 | 24.0 | 80 | 84.8 |
| 11 | 0.085 | 0.12 | 0.035 | 1.5 | 24.0 | 65 | 85.1 |
| 12 | 0.085 | 0.12 | 0.035 | 1.5 | 24.0 | 65 | 86.0 |
| 13 | 0.085 | 0.12 | 0.035 | 1.5 | 24.0 | 65 | 86.6 |
| 14 | 0.085 | 0.12 | 0.035 | 2.0 | 24.0 | 80 | 86.5 |
| 15 | 0.085 | 0.12 | 0.035 | 2.0 | 24.0 | 50 | 86.2 |
| 16 | 0.085 | 0.12 | 0.047 | 1.0 | 24.0 | 65 | 85.5 |
| 17 | 0.085 | 0.12 | 0.047 | 1.5 | 24.0 | 50 | 85.7 |
| 18 | 0.085 | 0.12 | 0.047 | 1.5 | 24.0 | 80 | 84.1 |
| 19 | 0.085 | 0.12 | 0.047 | 2.0 | 24.0 | 65 | 82.6 |
| 20$^c$ | 0.048 | 0.0528 | 0.1 | 0$^d$ | 5.0 | 90 | 85.4 |
| 21* | 0.10 | 0.15 | 0.11 | 2.25 | 22.0 | 65 | 58.0 |
| 22* | 0.10 | 0.15 | 0.11 | 2.25 | 22.0 | 65 | 57.8 |
| 23* | 0.10 | 0.15 | 0.11 | 2.25 | 22.0 | 65 | 61.8 |
| 24* | 0.10 | 0.20 | 0.2 | 0.5 | 22.0 | 50 | 68.2 |
| 25* | 0.10 | 0.10 | 0.2 | 4.0 | 22.0 | 50 | 43.7 |
| 26* | 0.10 | 0.20 | 0.2 | 4.0 | 22.0 | 80 | 27.3 |
| 27* | 0.10 | 0.10 | 0.2 | 0.5 | 22.0 | 80 | 35.0 |
| 28*$^c$ | 0.093 | 0.466 | 1.0 | 2.0 | 2.0 | 25–45 | 68.4 |
| 29*$^c$ | 0.0246 | 0.246 | 1.0 | 2.3 | 2.3 | 80 | 77.0 |

$^a$Mole % based on Grignard reagent.
$^b$The reaction time is the total of the addition time, plus the time the reaction was stirred at the reaction temperature after complete addition.
$^c$Grignard reagent added to bromobenzene/catalyst mixture. No internal standard in GLCP analysis.
$^d$Added at once.
*Outside the scope of this invention.

What is claimed is:

1. In a process for producing 3-chloro-2-methyl-[1,1'-biphenyl] by cross-coupling bromobenzene with 3-chloro-2-methylphenylmagnesium chloride in tetrahydrofuran using nickel(II) acetylacetonate as catalyst, the improvement therein which comprises using a catalytic amount of said catalyst in the range 0.02–0.04 mole percent based on said 3-chloro-2-methylphenylmagnesium chloride.

* * * * *